United States Patent
Kim et al.

(10) Patent No.: US 9,993,446 B2
(45) Date of Patent: Jun. 12, 2018

(54) BIGUANIDE DERIVATIVE, A PREPARATION METHOD THEREOF, AND A PHARMACEUTICAL COMPOSITION CONTAINING THE BIGUANIDE DERIVATIVE AS AN ACTIVE INGREDIENT

(71) Applicant: IMMUNOMET THERAPEUTICS INC., Cambridge, MA (US)

(72) Inventors: Sung Wuk Kim, Gyeonggi-do (KR); Sung Soo Jun, Gyeonggi-do (KR); Chang Hee Min, Seoul (KR); Young Woong Kim, Daejeon (KR); Min Seok Kang, Gyeonggi-do (KR); Byung Kyu Oh, Daejeon (KR); Se Hwan Park, Daejeon (KR); Yong Eun Kim, Daejeon (KR); Duck Kim, Daegu (KR); Ji Sun Lee, Daejeon (KR); Ju Hoon Oh, Gangwon-do (KR)

(73) Assignee: Immunomet Therapeutics Inc., Houston, TX (US)

( * ) Notice: Subject to any disclaimer, the term of this patent is extended or adjusted under 35 U.S.C. 154(b) by 0 days. days.

(21) Appl. No.: 15/206,780

(22) Filed: Jul. 11, 2016

(65) Prior Publication Data
US 2016/0317478 A1 Nov. 3, 2016

Related U.S. Application Data

(62) Division of application No. 13/520,902, filed as application No. PCT/KR2011/000097 on Jan. 6, 2011, now Pat. No. 9,416,098.

(30) Foreign Application Priority Data

Jan. 6, 2010 (KR) .................. 10-2010-0001021
Jan. 6, 2011 (KR) .................. 10-2011-0001438

(51) Int. Cl.

| | | |
|---|---|---|
| *A61K 31/155* | (2006.01) |
| *A61K 31/341* | (2006.01) |
| *A61K 31/4406* | (2006.01) |
| *A61K 31/472* | (2006.01) |
| *C07C 279/26* | (2006.01) |
| *C07C 277/04* | (2006.01) |
| *C07C 279/04* | (2006.01) |
| *C07C 279/06* | (2006.01) |
| *C07C 279/08* | (2006.01) |
| *C07C 279/16* | (2006.01) |
| *C07C 279/18* | (2006.01) |
| *C07D 213/38* | (2006.01) |
| *C07D 307/52* | (2006.01) |
| *C07D 317/58* | (2006.01) |
| *C07D 333/20* | (2006.01) |

(52) U.S. Cl.
CPC .......... *A61K 31/155* (2013.01); *A61K 31/341* (2013.01); *A61K 31/4406* (2013.01); *A61K 31/472* (2013.01); *C07C 277/04* (2013.01); *C07C 279/04* (2013.01); *C07C 279/06* (2013.01); *C07C 279/08* (2013.01); *C07C 279/16* (2013.01); *C07C 279/18* (2013.01); *C07C 279/26* (2013.01); *C07D 213/38* (2013.01); *C07D 307/52* (2013.01); *C07D 317/58* (2013.01); *C07D 333/20* (2013.01); *C07C 2601/08* (2017.05); *C07C 2601/14* (2017.05); *C07C 2601/18* (2017.05); *C07C 2603/74* (2017.05)

(58) Field of Classification Search
None
See application file for complete search history.

(56) References Cited

U.S. PATENT DOCUMENTS

| | | |
|---|---|---|
| 3,366,650 A | 1/1968 | Bernstein et al. |
| 3,960,949 A | 6/1976 | Ahrens et al. |
| 9,416,098 B2 | 8/2016 | Kim et al. |
| 2012/0283299 A1 | 11/2012 | Kim et al. |

FOREIGN PATENT DOCUMENTS

| | | |
|---|---|---|
| DE | 833959 | 7/1949 |
| EP | 0507317 | 1/1998 |
| GB | 607720 | 9/1948 |
| WO | WO 2001-91696 | 12/2001 |
| WO | WO 2009-113092 | 9/2009 |
| WO | WO 2009/148623 A2 * | 12/2009 |

OTHER PUBLICATIONS

Shapiro et al., "Hypoglycemic Agents. IV. $N^1,N^5$-Alkyl- and Aralkylbiguanides," J Am Chem Soc. 81:4635-9 (1959).

(Continued)

*Primary Examiner* — Zinna Northington Davis
(74) *Attorney, Agent, or Firm* — Clark+Elbing LLP

(57) ABSTRACT

A biguanide derivative compound with N1-N5 substitution, which is represented by Formula 1, or a pharmaceutically acceptable salt thereof a method of preparing the same, and a pharmaceutical composition containing the same as an active ingredient are provided. The biguanide derivative may exhibit excellent effect on activation of AMPKα and inhibition of cancer cell proliferation in a low dose, compared to conventional drugs, and thus, may be useful to treat diabetes mellitus, obesity, hyperlipidemia, hypercholesterolemia, fatty liver, coronary artery disease, osteoporosis, polycystic ovarian syndrome, metabolic syndrome, cancer, etc.

7 Claims, No Drawings

(56) References Cited

OTHER PUBLICATIONS

Carrington et al., "Synthetic Antimalarials, Part XLIX. The Structure and Synthesis of the Dihydrotriazine Metabolite of Proguanil", Journal of Chem. Soc., 1954, pp. 1017-1031.
Shaw et al., "The preparation of Certain Amino-Substituted Perfluoroalkyl-s-Triazines", J. Org. Chem., vol. 24, Nov. 30, 1959, pp. 1809-1811.
International Search Report dated Sep. 2, 2011 for International Patent Application No. PCT/KR2011/00097.
Indian Office Action for Application No. 1904/MUMNP/2012, dated Oct. 14, 2015, 2 pages.
Neelakantan, "Preparation of Some 1,5-Diaryl Biguanides", Dec. 1957, [Contribution from the Organic Chemistry Department, Indian Institute of Science] pp. 1587-1588.
Shapiro et al., "Hypoglycemic Agents. III. 1-3 N1-Alkyl-and Aralkylbiguanides", Jul. 20, 1959, [Contribution from the Research Laboratories of the U.S. Vitamin Corporation], vol. 81:3728-3736.

\* cited by examiner

BIGUANIDE DERIVATIVE, A PREPARATION METHOD THEREOF, AND A PHARMACEUTICAL COMPOSITION CONTAINING THE BIGUANIDE DERIVATIVE AS AN ACTIVE INGREDIENT

RELATED APPLICATIONS

This application is a divisional application of U.S. patent Ser. No. 13/520,902, filed on Jul. 6, 2012, entitled "BIGUANIDE DERIVATIVE, A PREPARATION METHOD THEREOF AND A PHARMACEUTICAL COMPOSITION CONTAINING THE BIGUANIDE DERIVATIVE AS AN ACTIVE INGREDIENT", which is a 35 U.S.C. § 371 national phase application of PCT/KR2011/000097 (WO2011/083998), filed on Jan. 6, 2011, entitled "BIGUANIDE DERIVATIVE AS AN ACTIVE INGREDIENT", which application claims the benefit of Korean Application No. 10-2011-0001438, filed Jan. 6, 2011 and Korean Application No. 10-2010-0001021, filed Jan. 6, 2010, each of which is incorporated herein by reference in its entirety.

TECHNICAL FIELD

The present invention relates to a biguanide derivative exhibiting excellent effects on activation of 5'-AMP-activated protein kinase(AMPK) and inhibition of cancer cell proliferation in a low dose compared to conventional drugs, a method of preparing the same, and a pharmaceutical composition containing the same as an active ingredient.

BACKGROUND ART

Diabetes mellitus, a disease characterized by continuous hyperglycemia, is a disorder that affects the metabolization of carbohydrates and lipids. It is a disease aggravated by bloodstream disorders caused by hyperglycemia and systemic complications caused by decreased utilization of sugar. Diabetes mellitus is induced by insulin deficiency or insulin resistance, and diabetes mellitus that occurs due to insulin resistance is called type 2 diabetes mellitus.

Type 2 diabetes mellitus is caused by a malfunctioning of insulin in delivering sugar into cells due to the reduction in the number of insulin receptors or defects in the signal transduction system through a receptor, a condition known as insulin resistance and Type 2 diabetes mellitus directly destroys blood vessels due to hyperinsulinemia and aggravates metabolic syndrome.

Many kinds of drugs have been used to treat type 2 diabetes mellitus However, except for biguanide metformin, drugs are only partly effective in lowering blood sugar and are not sufficient in effectively preventing serious complications such as loss of sight, paralysis, apoplexy, renal failure, peripheral neuropathy, foot ulcer, etc. For example, a sulfonylurea-based drug forces insulin to be secreted from the pancreas to lower blood sugar. The medicinal effects of the sulfonylurea-based drug disappear immediately. Also, the sulfonylurea-based drug induces an abnormal lipid metabolism, thereby resulting in arteriosclerosis, weight gain, and brain damage caused by hypoglycemia. In addition, a glitazone-based drug is used in combination with metformin because it resolves the problem of insulin resistance in adipose tissues but has a side effect of destroying the retinal vessels. For these reasons, use of the glitazone-based drug requires special attention.

Metformin does not induce hypoglycemia, but it overcomes the problem of insulin resistance in adipose tissues, liver tissues and muscle tissues, and it functions to drastically lower blood sugar and decrease the level of glycosylated hemoglobin.

In addition, metformin is known to activate an AMP-activated protein kinase that physiologically controls carbohydrate and lipid metabolism and is also reported to decrease blood sugar level, improve lipid condition, and normalize menstrual irregularity, ovulation and pregnancy. Moreover, it has been proven that when metformin is used to treat p53 gene-deficient cancer cells, metformin activates an AMPK enzyme of the cancer cells and changes the metabolic energy pathway, and therefore, the cancer cells finally die [Monica Buzzai et al., Systemic Treatment with the Antidiabetic drug Metformin Selectively Impairs p53-Deficient Tumor Cell Growth, Cancer Res 2007; 67:(14)] since they cannot adjust to the changed metabolic pathway.

In addition, Josie M M Evans reported a study concluding that a type 2 diabetes mellitus subject patient treated with metformin has a lower risk of cancer than a subject who has not been treated with metformin [Josie M M, Evans et al. BMJ. 2005, 330, 1304-1305]. Moreover, Samantha L. Browker reported that subjects with type 2 diabetes mellitus who take metformin orally have a lower cancer mortality rate than subjects who take sulfonylurea orally or are administered with insulin [Samantha L et al., Diabetes mellitus Care. 2006, 29, 254-258].

There is an increasing amount of clinical evidence indicating hat a cancer stem cell is involved in the recurrence and metastasis of cancer. The content of cancer stem cells in a tumor tissue is 0.2% or less, but the cancer stem cells may not be removed by conventional anticancer chemotherapy. Metformin has an anticancer effect on cancer stem cells and excellent tolerability. In recent research relating to metformin, it has been reported that when doxorubicin, which is an anticancer drug, is administered alone, there is little change in cancer stem cells, but when administered together with metformin, it removes cancer stem cells [Heather A. Hirsch et al., Metformin Selectively Targets Cancer Stem Cells, and Acts Together with Chemotherapy to Block Tumor Growth and Prolong Remission, Cancer Res 2009; 69: (19) Oct. 1, 2009].

However, metformin is generally administered three times a day, and a single dose is approximately 500 mg or more. Thus, to prepare metformin as a sustained-released tablet to be administered once a day, the tablet should contain approximately 1,500 mg or more of metformin, but such a tablet is too large for most subjects to take. In addition, since extended release formulation available in the current market contains only approximately 750 mg of metformin, at least two tablets should be taken. For these reasons, a metformin-based substance exhibiting better pharmacological action than conventional metformin and having improved physiochemical characteristics is needed.

DISCLOSURE

Technical Problem

The present invention is directed to provide a novel biguanide derivative or a pharmaceutically acceptable salt thereof, which exhibits excellent effects on activation AMPK activation and inhibition of cancer cell proliferation in a small amount, compared to conventional drugs, and a method of preparing the same.

The present invention is also directed to provide a pharmaceutical composition containing the above-mentioned compound as an active ingredient to treat diabetes mellitus, obesity, hyperlipidemia, hypercholesterolemia, fatty liver, coronary artery disease, osteoporosis, polycystic ovarian syndrome, metabolic syndrome, cancer, etc.

Technical Solution

One aspect of the present invention provides a biguanide derivative compound with N1-N5 substitution, represented by Formula 1, or a pharmaceutically acceptable salt thereof.

[Formula 1]

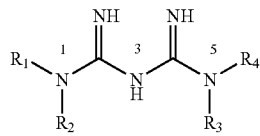

In Formula 1, $R_1$, $R_2$, $R_3$ and $R_4$ are independently hydrogen or a non-hydrogen substituent selected from the group consisting of $C_{1-12}$ alkyl unsubstituted or substituted with at least one non-hydrogen substituent selected from the group consisting of $C_{3-10}$ cycloalkyl, $C_{5-12}$ aryl, $C_{5-12}$ heteroaryl, hydroxyl, halogen and $C_{1-4}$ alkoxycarbonyl; $C_{3-10}$ cycloalkyl; $C_{1-12}$ alkoxy; $C_{5-12}$ aryl; $C_{5-12}$ heteroaryl; hydroxyl and halogen, and the aryl and heteroaryl are unsubstituted or substituted with at least one non-hydrogen substituent selected from the group consisting of $C_{1-4}$ alkyl, $C_{1-4}$ alkoxy, hydroxyl and halogen.

A "substituted" group used herein is a group in which at least one hydrogen atom is replaced with at least one non-hydrogen atom group, provided that the group has to satisfy a requirement of valence and generate a chemically stable compound from the substitution. In the specification, unless explicitly described as "unsubstituted," it should be understood that all of substituents may be substituted or unsubstituted. $R_1$ to $R_4$ substituents on the biguanide according to the present invention may each be substituted again with at least one of the above-defined substituents.

"Alkyl" refers to a linear and branched saturated hydrocarbon group, generally having a specified number of carbon atoms (for example, 1 to 12 carbon atoms). Examples of the alkyl group include, without limitation, methyl, ethyl, n-propyl, isopropyl, n-butyl, sec-butyl, isobutyl, tert-butyl, n-pentyl, n-hexyl and n-heptyl. The alkyl may be attached to a parent group or a substrate at any ring atom, unless such attachment would violate valence requirements. Likewise, the alkyl or alkenyl group may include at least one non-hydrogen substituent unless such substitution would violate valence requirements.

"Cycloalkyl" refers to saturated monocyclic and polycyclic hydrocarbon rings, generally having a specified number of carbon atoms that include the ring (for example, $C_{3-10}$ cycloalkyl refers to a cycloalkyl group having 3, 4, 5, 6, 7, 8, 9, or 10 carbon atoms as ring members). The cycloalkyl may be attached to a parent or substrate at any ring atom, unless such attachment would violate valence requirements. Likewise, the cycloalkyl group may include at least one non-hydrogen substituent unless such substitution would violate valence requirements.

"Aryl" refers to monovalent and bivalent aromatic groups, respectively including 5- and 6-membered monocyclic aromatic groups and "heteroaryl" refers to monovalent and bivalent aromatic groups, respectively including 5- and 6-membered monocyclic aromatic groups that contain 1 to 4 heteroatoms independently selected from nitrogen, oxygen and sulfur. Examples of the monocyclic aryl group and heteroaryl group include, without limitation, phenyl, pyridinyl, furanyl, pyrrolyl, thiopheneyl, thiazolyl, isothiazolyl, imidazolyl, triazolyl, tetrazolyl, pyrazolyl, oxazolyl, isoxazolyl, pyrazinyl, pyridazinyl, pyrimidinyl, etc. The aryl and heteroaryl groups also include bicyclic groups, tricyclic groups, etc., including fused 5- and 6-membered rings as described above. Examples of the polycyclic aryl and heteroaryl groups include, without limitation, isoquinolinyl, naphthyl, biphenyl, anthracenyl, pyrenyl, carbazolyl, benzoxazolyl, benzodioxazolyl, benzothiazolyl, benzoimidazolyl, benzothiopheneyl, quinolinyl, indolyl, benzofuranyl, purinyl, indolizinyl, etc. The aryl and heteroaryl groups may be attached to a parent group or to a substrate at any ring atom, unless such attachment would violate valence requirements. Likewise, the aryl and heteroaryl groups may include at least one non-hydrogen substituent unless such substitution would violate valence requirements. Non-hydrogen substituents of the acryl and heteroaryl groups may also be substituted with additional non-hydrogen substituents.

"Carbonyl" refers to —C(O)R'. "(O)" used herein refers to an oxygen binding to an atom such as carbon or sulfur by a double bond. Here, "R'" refers to non-hydrogen substituents such as lower alkyl, lower alkoxy, etc. Examples of the carbonyl group include, without limitation, 2-methoxyoxoethyl, 3-methoxyoxopropyl, etc. The carbonyl group may be attached to a parent group or to a substrate at any ring atom, unless such attachment would violate valence requirements. Likewise, the carbonyl group may include at least one non-hydrogen substituent unless such substitution would violate valence requirements.

"Alkoxy" refers to alkyl-O—. Here, the alkyl is defined above. Examples of the alkoxy group include, without limitation, methoxy, ethoxy, etc. The alkoxy may be attached to a parent group or to a substrate at any ring atom, unless such attachment would violate valence requirements. Likewise, the alkoxy group may include at least one non-hydrogen substituent unless such substitution would violate valence requirements.

"Hydroxyl" refers to —OH, "halogen" refers to fluoro, chloro, bromo, and iodo, and "oxo" refers to =O.

In the compound of Formula 1 of the present invention, $R_1$, $R_2$, $R_3$ and $R_4$ are independently hydrogen or a non-hydrogen substituent selected from the group consisting of $C_{1-12}$ alkyl; $C_{3-10}$ cycloalkyl; $C_{1-12}$ alkoxy; $C_{5-12}$ aryl; $C_{5-12}$ heteroaryl; hydroxyl and halogen.

Here, the $C_{1-12}$ alkyl may be a linear or branched $C_{1-12}$ alkyl unsubstituted or substituted with at least one non-hydrogen substituent. When the alkyl is substituted with a non-hydrogen substituent, the alkyl may be, but is not limited to, a linear or branched alkyl having 1 to 12 carbon atoms. Here, non-hydrogen substituents for the alkyl may be selected from the group consisting of $C_{3-10}$ cycloalkyl, $C_{5-12}$ aryl, $C_{5-12}$ heteroaryl, hydroxyl, halogen and $C_{1-4}$ alkoxycarbonyl, but the present invention is not limited thereto. The non-hydrogen substituents may also be further substituted or unsubstituted. For example, the aryl and heteroaryl may be unsubstituted or substituted with at least one non-hydrogen substituent selected from the group consisting of $C_{1-4}$ alkyl, $C_{1-4}$ alkoxy, hydroxyl and halogen.

In one embodiment, $R_1$, $R_2$, $R_3$ and $R_4$ are independently hydrogen or a non-hydrogen substituent selected from the group consisting of unsubstituted $C_{1-2}$ alkyl; $C_{1-6}$ alkyl substituted with at least one non-hydrogen substituent selected from the group consisting of unsubstituted $C_{3-7}$ cycloalkyl, $C_{5-12}$ aryl, $C_{5-12}$ heteroaryl, hydroxyl, halogen and $C_{1-4}$ alkoxycarbonyl; unsubstituted $C_{3-7}$ cycloalkyl; $C_{1-6}$ alkoxy; $C_{5-12}$ aryl; $C_{5-12}$ heteroaryl; hydroxyl; and halogen. The aryl and heteroaryl may be unsubstituted or substituted with at least one non-hydrogen substituent selected from the group consisting of $C_{1-4}$ alkyl, $C_{1-4}$ alkoxy, hydroxyl and halogen.

In one embodiment, $R_1$ and $R_4$ are independently non-hydrogen substituents selected from the group consisting of unsubstituted $C_{1-7}$ alkyl; $C_{1-6}$ alkyl substituted with at least one non-hydrogen substituent selected from the group consisting of unsubstituted $C_{3-7}$ cycloalkyl, $C_{5-12}$ aryl, $C_{5-12}$ heteroaryl and $C_{1-4}$ alkoxycarbonyl; unsubstituted $C_{3-7}$ cycloalkyl; $C_{5-12}$, aryl; and $C_{5-12}$ heteroaryl, $R_2$ and $R_3$ are hydrogen; unsubstituted $C_{1-7}$ alkyl; $C_{5-12}$ aryl; or $C_{1-6}$ alkyl substituted with $C_{5-12}$ heteroaryl, and the aryl and heteroaryl may be unsubstituted or substituted with at least one non-hydrogen substituent selected from the group consisting of $C_{1-4}$ alkyl, $C_{1-4}$ alkoxy, hydroxyl and halogen.

In one embodiment, $R_1$ and $R_4$ are independently non-hydrogen substituents selected from the group consisting of unsubstituted $C_{1-7}$ alkyl; $C_{1-4}$ alkyl substituted with at least one non-hydrogen substituent selected from the group consisting of unsubstituted $C_{3-7}$ cycloalkyl, $C_{5-12}$ aryl, $C_{5-12}$ heteroaryl and $C_{1-4}$ alkoxycarbonyl; unsubstituted $C_{3-7}$ cycloalkyl; $C_{5-12}$ aryl; and $C_{5-12}$ heteroaryl, $R_2$ and $R_3$ are hydrogen; unsubstituted $C_{1-7}$ alkyl; $C_{5-12}$ aryl; or $C_{1-4}$ alkyl substituted with $C_{5-12}$ heteroaryl, and the aryl and heteroaryl may be unsubstituted or substituted with at least one non-hydrogen substituent selected from the group consisting of $C_{1-4}$ alkoxy, hydroxyl and halogen, or may be selected from the group consisting of phenyl, pyridinyl, furanyl and isoquinolinyl.

In one embodiment, $R_1$ is unsubstituted $C_{1-7}$ alkyl; $C_{1-4}$ alkyl substituted with $C_{5-12}$ aryl or $C_{5-12}$ heteroaryl; $C_{5-12}$ aryl; or $C_{5-12}$ heteroaryl, $R_2$ is hydrogen; or unsubstituted $C_{1-7}$ alkyl, $R_3$ is hydrogen; unsubstituted $C_{1-7}$ alkyl; $C_{5-12}$ aryl; or $C_{5-12}$ heteroaryl, and $R_4$ is a non-hydrogen substituent selected from the group consisting of unsubstituted $C_{1-7}$alkyl; $C_{1-4}$ alkyl substituted with at least one non-hydrogen substituent selected from the group consisting of unsubstituted $C_{3-7}$ cycloalkyl, $C_{5-12}$ aryl, $C_{5-12}$ heteroaryl and $C_{1-4}$ alkoxycarbonyl; unsubstituted $C_{3-7}$ cycloalkyl; $C_{5-12}$ aryl; and $C_{5-12}$ heteroaryl. The aryl and heteroaryl may be unsubstituted or substituted with at least one non-hydrogen substituent selected from the group consisting of $C_{1-4}$ alkoxy, hydroxyl and halogen, or may be selected from the group consisting of phenyl, pyridinyl, furanyl and isoquinolinyl.

In one embodiment, the compound of Formula 1 may be N1-hexyl-N5-propyl biguanide; N1-propyl-N5-cyclopropylmethyl biguanide; N1-hexyl-N5-cyclohexylmethyl biguanide; N1-hexyl-N5-benzyl biguanide; N1,N5-bis(4-chlorophenyl) biguanide; N1,N5-bis(3-chlorophenyl) biguanide; N1-(4-chloro)phenyl-N5-(4-methoxy)phenyl biguanide; N1,N5-bis(3-chloro-4-methoxyphenyl) biguanide; N1,N5-bis(3,4-dichlorophenyl) biguanide; N1,N5-bis(3,5-dichlorophenyl) biguanide; N1,N5-bis(4-bromophenyl) biguanide; N1-benzyl-N5-(pyridine-3-yl)methyl biguanide; N1-(phenethyl)-N5-propyl biguanide; N1-(phenethyl)-N5-cyclopropylmethyl biguanide; N1-(phenethyl)-N5-cycloheptyl biguanide; N1,N5-bis(phenethyl) biguanide; N1,N1,N5-trimethyl biguanide; N1,N1-dimethyl-N5-butyl biguanide; N1,N1-dimethyl-N5-(butane-2-yl) biguanide; N1,N1-dimethyl-N5-t-butyl biguanide; N1,N1-dimethyl-N5-pentyl biguanide; N1,N1-dimethyl-N5-methoxycarbonylethyl biguanide; N1,N1-dimethyl-N5-cycloheptyl biguanide; N1,N1-dimethyl-N5-cyclopropylmethyl biguanide; N1,N1-dimethyl-N5-(4-bromo)phenyl biguanide; N1,N1-dimethyl-N5-(furan-2-yl)methyl biguanide; N1,N1-dimethyl-N5-pyridine-3-yl)methyl biguanide; N1,N1-dimethyl-N5-benzyl biguanide; N1,N1-dimethyl-N5-(phenethyl) biguanide; N1,N1-diethyl-N5-(3-chloro)phenyl biguanide; N1,N1-dipropyl-N5-(3-chloro)phenyl biguanide; N1,N1-(ethyl)(propyl)-N5-(4-chloro)phenyl biguanide; N1,N1-dipropyl-N5-(isoquinoline-5-yl) biguanide; N1,N1-dihexyl-N5-(3-chloro)phenyl biguanide; N1,N1,N5,N5-tetraethyl biguanide; N1,N1-diethyl-N5,N5-(cyclohexyl)(methyl) biguanide; N1,N1-dipropyl-N5,N5-diethyl biguanide; N1,N1-dipropyl-N5,N5-(methyl)(phenethyl) biguanide; N1,N1-dipropyl-N5,N5-(4-hydroxylphenyl)(phenyl) biguanide; or N1,N1,N5,N5-bis((benzyl)(methyl)) biguanide.

Meanwhile, the pharmaceutically acceptable salt of the compound of Formula 1 according to the present invention may be an acid addition salt formed using an organic acid or inorganic acid. Examples of the organic acid include formic acid, acetic acid, propionic acid, lactic acid, butyric acid, isobutyic acid, trifluoroacetic acid, malic acid, maleic acid, malonic acid, fumaric acid, succinic acid, succinic acid monoamide, glutamic acid, tartaric acid, oxalic acid, citric acid, glycolic acid, glucuronic acid, ascorbic acid, benzoic acid, phthalic acid, salicylic acid, anthranyl acid, dichloroacetic acid, aminooxy acetic acid, benzenesulfonic acid, p-toluenesulfonic acid and methanesulfonic acid, and examples of the inorganic acid include hydrochloric acid, bromic acid, sulfuric acid, phosphoric acid, nitric acid, carbonic acid and boric acid. The above-mentioned acid addition salt may be prepared by a general method of preparing a salt, including a) directly mixing the compound of Formula 1 and an acid, b) dissolving one of the compound and an acid in a solvent or a hydrated solvent and mixing the resulting solution with the other element, or c) dissolving the compound of and an acid in a solvent or a hydrated solvent, respectively, and mixing them.

When the compound of Formula 1 has an acid group such as a carboxyl group and a sulfonic group, the compound may become an zwitterionic salt, and examples of the salt may include alkali metal salts (i.e., a sodium salt, a potassium salt, etc.), alkali earth metal salts (i.e., a calcium salt, a magnesium salt, etc.), inorganic acid-based salts (i.e., an aluminum salt, an ammonium salt, etc.), and basic addition salts (i.e., trimethyl amine, triethyl amine, pyridine, picoline, ethanolamine, diethanolamine, triethanolamine, dicyclohexyl amine, N,N'-dibenzylethylenediamine-based salt, etc.). In addition, the salt of the compound of Formula 1 may be a basic amino acid-based salt (i.e., an arginine, lysine, or ornitine-based salt) or an acidic amino acid-based salt (i.e., an aspartame-based salt).

In one embodiment, the pharmaceutically acceptable salt of the compound of Formula 1 may be a salt with an acid selected from the group consisting of formic acid, acetic acid, propionic acid, lactic acid, butyric acid, isobutyic acid, trifluoroacetic acid, malic acid, maleic acid, malonic acid, fumaric acid, succinic acid, succinic acid monoamide, glutamic acid, tartaric acid, oxalic acid, citric acid, glycolic acid, glucuronic acid, ascorbic acid, benzoic acid, phthalic acid, salicylic acid, anthranyl acid, benzenesulfonic acid, p-toluenesulfonic acid, methanesulfonic acid, dichloroacetic acid, aminooxy acetic acid, hydrochloric acid, bromic acid, sulfuric acid, phosphoric acid, nitric acid, carbonic acid and boric acid.

The compound of Formula 1 according to the present invention may be prepared by multiple methods.

In one embodiment, a method of preparing the compound of Formula 1 includes reacting a compound of Formula 2 with a dicyanoamide in at least one organic solvent to obtain a compound of Formula 3; and reacting the compound of Formula 3 with a compound of Formula 4 in at least one organic solvent to obtain the compound of Formula 1.

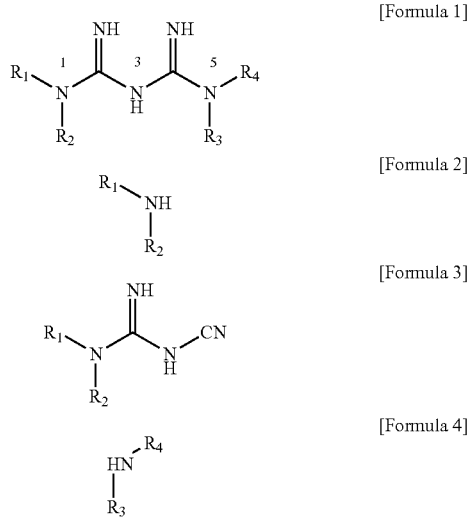

[Formula 1]

[Formula 2]

[Formula 3]

[Formula 4]

In these formulas, $R_1$, $R_2$, $R_3$ and $R_4$ are the same as defined in Formula 1. The method may be illustrated in Reaction Scheme 1, and will be described in steps.

[Reaction Scheme 1]

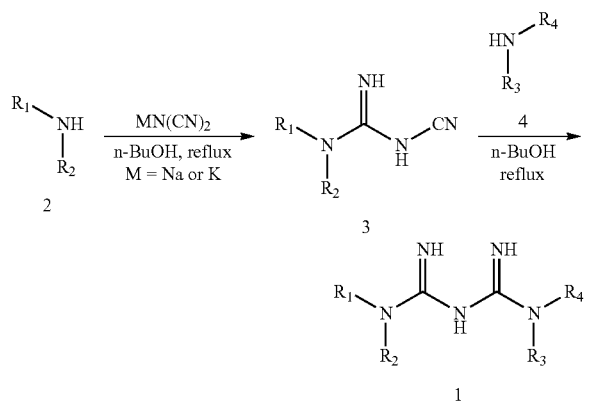

In the method of preparing the compound of Formula 1, the cyanoguanidine compound of Formula 3 used as an intermediate may be prepared by reacting substituted amine of Formula 2 with a dicyanoamide such as sodium or potassium dicyanoamide in at least one organic solvent to convert the substituted amine into the cyanoguanidine compound of Formula 3 and then refluxing the cyanoguanidine compound of Formula 3 with the compound of Formula 4 in at least one organic solvent.

An amount of the sodium cyanoamide used in the preparation of the cyanoguanidine compound of Formula 3 is equivalent to approximately 1 to 2 moles with respect to the compound of Formula 2, and examples of the organic solvent used herein may be ethanol, isopropanol, n-butanol, t-butanol, etc. The reaction temperature is in the range of 60 to 150° C.

After the cyanoguanidine compound of Formula 3 obtained above is dissolved in at least one organic solvent (i.e., ethanol, isopropanol, n-butanol or 1,4-dioxane), the compound of Formula 4 is added and then refluxed stirring. Here, an amount of the compound of Formula 4 is equivalent to approximately 1 to 2 moles with respect to the compound of Formula 3, and the reaction temperature is in the range of the reflux temperature of the solvent used (i.e., room temperature to 140° C. for butanol). When the reaction is completed, the resulting product is filtered, and the pH of the reaction solution is controlled to approximately 4 to 5 using an acid, such as hydrochloric acid. A solution produced as such is concentrated and purified, thereby yielding the compound of Formula 1 or a pharmaceutically acceptable salt thereof.

Compared to conventional drugs, only a small amount of the compound of Formula 1 or the pharmaceutically acceptable salt thereof produced as such may exhibit effects on activation of AMPK and inhibition of cancer cell proliferation, which can be confirmed in the following example. It is known that AMPK activation inhibits cancer, decreases blood sugar, and lowers lipid concentration, as described above. Therefore, the compound of Formula 1 or the pharmaceutically acceptable salt thereof may be useful to treat diabetes mellitus, obesity, hyperlipidemia, hypercholesterolemia, fatty liver, coronary artery disease, osteoporosis, polycystic ovarian syndrome, metabolic syndrome, etc., as well as cancer.

Another aspect of the present invention provides a drug comprising the compound of Formula 1 or the pharmaceutically acceptable salt thereof as an active ingredient.

Still another aspect of the present invention provides a pharmaceutical composition comprising a compound of Formula 1 or a pharmaceutically acceptable salt thereof as an active ingredient to treat a disease selected from the group consisting of diabetes mellitus, obesity, hyperlipidemia, hypercholesterolemia, fatty liver, coronary artery disease, osteoporosis, polycystic ovarian syndrome, metabolic syndrome, cancer, muscle pain, myocyte damage and rhabdomyolysis, a use of the compound of Formula 1 or the pharmaceutically acceptable salt thereof to treat the above-mentioned disease, and a method of treating the disease including administering a therapeutically effective amount of the compound of Formula 1 or the pharmaceutically acceptable salt thereof to a subject.

In one embodiment, diabetes mellitus may be non-insulin dependent diabetes mellitus.

In one embodiment, the cancer may be breast cancer, colorectal cancer, gastric cancer, liver cancer, lung cancer, blood cancer, prostate cancer, brain cancer, pancreatic cancer, ovarian cancer, or endometrial cancer.

The pharmaceutical composition of the present invention comprises at least one pharmaceutically acceptable carrier in addition to an ac re ingredient. As used in the present invention, "pharmaceutically acceptable carrier" refers to a known pharmaceutically acceptable excipient, which is useful to formulate a pharmaceutically active compound for administration to a subject, and is substantially non-toxic and non-sensitive under the conditions it is used. An exact ratio of the excipient is determined by standard pharmaceutical practice, as well as solubility, chemical characteristics and selected route of administration of the active compound.

The pharmaceutical composition of the present invention may be formulated in a suitable type for a desired administration method using adjuvants such as a excipient, a disintegrating agent, a sweetening agent, a binder, a coating agent, a swelling agent, a lubricating agent, a glossing agent, a flavoring agent, etc, which are suitable and physiologically acceptable.

The pharmaceutical composition may be formulated as a tablet, a capsule, a pill, a granule, powder, an injection or a liquid, but is not limited thereto.

Meanwhile, in the present invention, "subject" refers to warm-blooded animals such as mammals with a specific disease, disorder or illness, for example, including humans, orangutans, mice, rats, dogs, cows, chickens, pigs, goats, sheep, etc., but the present invention is not limited thereto.

In addition, "treating" includes relieving a symptom temporarily or permanently, eliminating a cause of the symptom, and preventing or lowering occurrence of the symptom, progression of the disease, disorder or illness, but the present invention is not limited thereto.

An effective amount of the active ingredient of the pharmaceutical composition of the present invention refers to an amount required for treating a disease. Therefore, the effective amount may be controlled by various factors such as type and severity of a disease, kinds and contents of an active ingredient and other ingredients contained in the composition, a type of formulation, age, body weight, general medical conditions, sex and diet of a subject, duration and route for administration, release rate of the composition, treatment regime, and drugs simultaneously used. For example, to a male adult having a body weight of 60 kg, the compound of Formula 1 may be administered once to several times a day in a dosage range from 0.5 to 100 mg/kg of body weight. However, the dosage may vary depending on various factors listed above, and in some cases, a smaller or larger amount than the above-mentioned dosage of the composition may be administered.

Advantageous Effects

A biguanide derivative of Formula 1 according to the present invention can exhibit excellent effects on activation of AMPK and inhibition of cancer cell proliferation in a low dose compared to conventional drugs, and thus, can be useful to treat diabetes mellitus, obesity, hyperlipidemia, hypercholesterolemia, fatty liver, coronary artery disease, osteoporosis, polycystic ovarian syndrome, metabolic syndrome, cancer, etc.

BEST MODE

The advantages and features of the present invention and the method of revealing them will be explicit from the following examples described in detail. However, it is to be distinctly understood that the present invention is not limited thereto but may be otherwise variously embodied and practiced. It is obvious that the following examples are to complete the disclosure of the invention and to indicate the scope of the present invention to a skilled artisan completely, and the present invention will be defined only by the scope of the claims.

EXAMPLES

Example 1: Preparation of N1-hexyl-N5-propyl biguanide hydrochloride

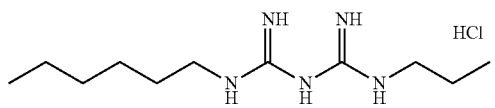 [SMILES: CCCCCCNC(=N)NC(=N)NCCC ; Cl]

(1-1) Synthesis of 1-hexyl-3-cyanoguanidine

While a solution prepared by dissolving 1-hexyl amine (3.6 g, 35.9 mmol) in n-butanol (30 ml) was stirred, sodium dictanoamide (3.5 g, 39.5 mmol) and concentrated hydrochloric acid (3.4 ml, 39.5 mmol) were added thereto at room temperature. The mixed solution was refluxed with stirring for 24 hours. After confirming the completion of the reaction, the generated sodium chloride was removed by filtering the reaction mixture, and then the filtered solution was concentrated under reduced pressure. After the concentrate was filtered, the filter-cake was washed with distilled water (30 ml). The filter-cake was vacuum-dried, thereby obtaining a target compound as a white solid (3.4 g, 58%). The compound was used in a subsequent reaction without another step of purification.

(1-2) Preparation of N1-hexyl-N5-propyl biguanide hydrochloride

Concentrated hydrochloric acid (0.47 ml, 5.31 mmol) was added to a solution prepared by dissolving 1-propyl amine (0.58 g, 5.84 mmol) in n-butanol (10 ml), and the mixed solution was stirred for 30 minutes at room temperature. The compound obtained in the previous step (1-1) (0.89 g, 5.31 mmol) was added to the reaction mixture and refluxed with stirring for 24 hours. The mixture was concentrated under reduced pressure, and the concentrate was purified using flash column chromatography (dichloromethane:methanol=9:1). A 6N methanol hydrochloride solution (1 ml) was added to the compound to dissolve, and the mixture was concentrated under reduced pressure, thereby obtaining a target compound as a white solid (0.92 g, 65%).

$^1$H NMR (600 MHz, DMSO-$d_6$) δ 7.46 (br s, 2H), 6.81 (br s, 2H), 3.05 (m, 4H), 1.44 (m, 4H) 1.25 (m, 6H), 0.85 (t, 3H, J=7.2 Hz); mp 148-149° C.

Target compounds of the following Examples 2 to 40 were prepared by the same method as described in Example 1, except that an amine compound corresponding to the target compound was used instead of 1-hexyl amine and 1-propyl amine respectively used in steps (1-1) and (1-2) of Example 1.

Example 2: N1-propyl-N5-cyclopropylmethyl biguanide hydrochloride

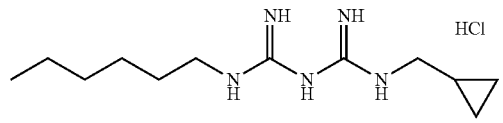 [SMILES: CCCCCCNC(=N)NC(=N)NCC1CC1 ; Cl]

$^1$H NMR (600 MHz, DMSO-$d_6$) δ 7.50 (br s, 2H), 6.83 (br s, 3H), 3.07 (m, 2H), 2.97 (m, 2H), 1.42 (m, 2H), 1.26 (m, 6H), 0.95 (m, 1H), 0.85 (t, 3H, J=6.6 Hz), 0.42 (m, 2H), 0.17 (d, 2H, J=4.8 Hz); mp 162-163° C.

Example 3: N1-hexyl-N5-cyclohexylmethyl biguanide hydrochloride

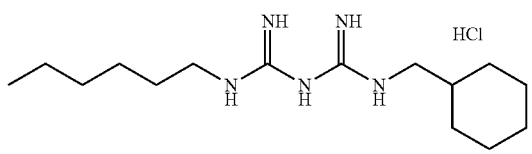 [SMILES: CCCCCCNC(=N)NC(=N)NCC1CCCCC1 ; Cl]

$^1$H NMR (600 MHz, DMSO-d$_6$) δ 8.22 (br s, 2H), 3.12 (m, 2H), 2.73 (dd, 2H, J=7.5, 7.2 Hz), 1.96 (m, 2H), 1.68 (m, 2H), 1.50-1.59 (m, 7H), 1.46 (m, 2H), 1.38 (m, 2H), 1.23-1.36 (m, 4H), 0.87 (t, 3H, J=7.2 Hz)

Example 4: N1-hexyl-N5-benzyl biguanide hydrochloride

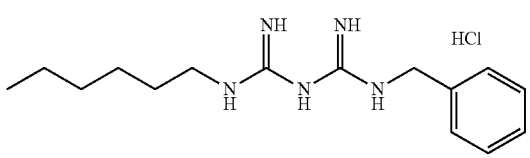 [SMILES: CCCCCCNC(=N)NC(=N)NCc1ccccc1 ; Cl]

$^1$H NMR (600 MHz, DMSO-d$_6$) δ 8.45 (br s, 1H), 7.24-7.36 (m, 5H), 6.92 (br s, 2H), 4.33 (d, 2H, J=6.0 Hz), 3.08 (m, 2H), 1.21-1.44 (m, 8H), 0.86 (m, 3H): mp 121-123° C.

Example 5: N1,N5-bis(4-chlorophenyl) biguanide hydrochloride

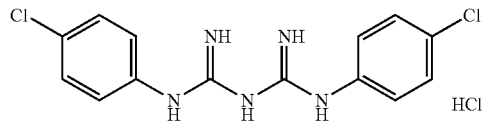 [SMILES: N=C(NC(=N)Nc1ccc(Cl)cc1)Nc1ccc(Cl)cc1 ; Cl]

$^1$H NMR (600 MHz, DMSO-d$_6$) δ 10.02 (br s, 2H), 7.54 (br s, 2H), 7.38 (d, 4H, J=9.0 Hz), 7.32 (d, 4H, J=9.0 Hz); mp 263-264° C.

Example 6: N1,N5-bis(3-chlorophenyl) biguanide hydrochloride

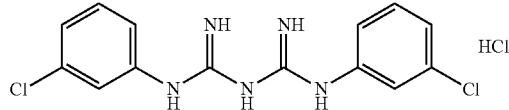 [SMILES: N=C(NC(=N)Nc1cccc(Cl)c1)Nc1cccc(Cl)c1 ; Cl]

$^1$H NMR (400 MHz, DMSO-d$_6$) δ 9.23 (br s, 2H), 7.54 (dd, 2H, J=2.0, 2.0 Hz), 7.32 (dd, 2H, J=8.2, 8.2 Hz), 7.23 (ddd, 2H, J=8.2, 2.0, 0.8 Hz), 7.15 (br s, 2H), 7.11 (ddd, 2H, J=8.2, 2.0, 0.8 Hz); mp 129-131° C.

Example 7: N1-(4-chloro)phenyl-N5-(4-methoxy)phenyl biguanide hydrochloride

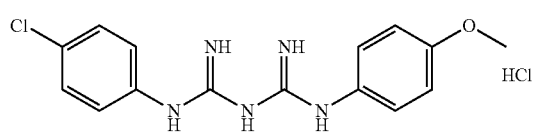 [SMILES: COc1ccc(NC(=N)NC(=N)Nc2ccc(Cl)cc2)cc1 ; Cl]

$^1$H NMR (600 MHz, DMSO-d$_6$) δ 9.87 (br s, 9.75 (br s, 1H), 7.49 (br s, 1H), 7.35 (d, 2H, J=9.0 Hz), 7.33 (d, J=9.0 Hz), 7.30 (br s, 1H), 7.20 (d, 2H, 9.0 Hz), 6.91 (d, 2H, 9.0 Hz), 3.72 (s, 3H); mp 247-249° C.

Example 8: N1,N5-bis(3-chloro-4-methoxyphenyl) biguanide hydrochloride

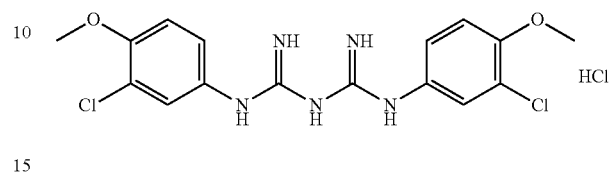

$^1$H NMR (600 MHz, DMSO-d$_6$) δ 9.11 (br s, 1H), 7.46 (d, 2H, J=2.4 Hz), 7.20 (dd, 2H, J=9.0, 2.4 Hz), 7.09 (d, 2H, J=9.0 Hz), 7.05 (br s, 1H), 3.83 (s, 6H); mp 203-204° C.

Example 9: N1,N5-bis(3,4-dichlorophenyl) biguanide hydrochloride

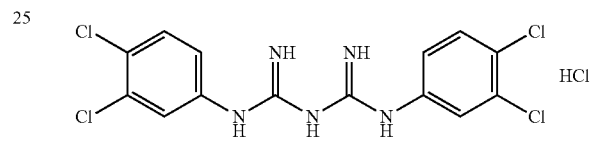

$^1$H NMR (600 MHz, DMSO-d$_6$) δ 10.3 (br s, 1H), 7.73 (br s, 1H), 7.63 (s, 2H), 7.59 (d, 2H, J=9.0 Hz), 7.28 (d, 2H, J=9.0 Hz); mp 255-257° C.

Example 10: N1,N5-bis(3,5-dichlorophenyl) biguanide hydrochloride

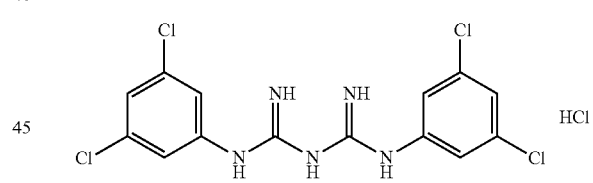

$^1$H NMR (600 MHz, DMSO-d$_6$) δ 10.48 (br s, 1H), 7.85 (br s, 1H), 7.40 (d, 4H, J=1.8 Hz), 7.35 (d, 2H, J=1.8 Hz); mp 250-251° C.

Example 11: N1,N5-bis(4-bromophenyl) biguanide hydrochloride

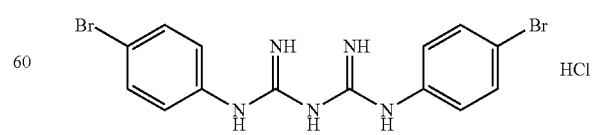

$^1$H NMR (600 MHz, DMSO-d$_6$) δ 10.17 (br s, 7.59 (br s, 1H), 7.49 (d, 4H, J=7.2 Hz), 7.27 (d, 4H, J=7.2 Hz); mp 242-243° C.

Example 12: N1-benzyl-N5-(pyridine-3-yl)methyl biguanide hydrochloride

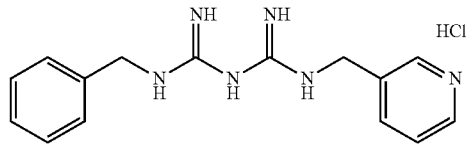 [SMILES: N=C(NCc1ccccc1)NC(=N)NCc1cccnc1 ; Cl]

$^1$H NMR (400 MHz, DMSO-d$_6$) δ 8.67 (s, 1H), 8.57 (dd, 1H, J=4.8, 1.6 Hz), 8.45 (br s, 2H), 7.93 (dd, 1H, J=7.6, 1.6 Hz), 7.90 (br a, 1H), 7.45 (dd, 1H, J=7.6, 4.8 Hz), 7.18-7.34 (m, 5H), 7.21 (br s, 1H), 4.32 (m, 2H), 4.06 (s, 2H); mp 138-140° C.

Example 13: N1-(phenethyl)-N5-propyl biguanide hydrochloride

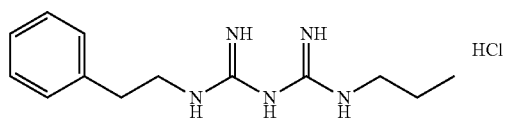 [SMILES: CCCNC(=N)NC(=N)NCCc1ccccc1 ; Cl]

$^1$H NMR (400 MHz, DMSO-d$_6$) 7.33 (br s, 2H), 7.21-7.37 (m, 5H), 6.87 (br s, 2H), 3.33 (m, 2H), 2.79 (m, 2H), 1.46 (m, 2H), 0.87 (t, 3H, J=7.2 Hz); mp 126-128° C.

Example 14: N1-(phenethyl)-N5-cyclopropylmethyl biguanide hydrochloride

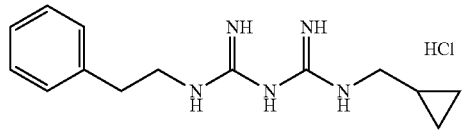 [SMILES: N=C(NCCc1ccccc1)NC(=N)NCC1CC1 ; Cl]

$^1$H NMR (600 MHz. DMSO-d$_6$) δ 7.20-7.32 (m, 5H), 3.32 (m, 2H), 2.98 (t, 2H, J=6.0 Hz), 2.76 (m, 2H), 0.96 (m, 1H), 0.41 (dd, 2H, J=7.8, 1.8 Hz), 0.19 (dd, 2H, J=4.8, 1.8 Hz); mp 143-146° C.

Example 15: N1-(phenethyl)-N5-cycloheptyl biguanide hydrochloride

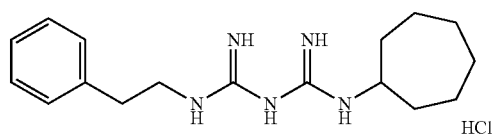 [SMILES: N=C(NCCc1ccccc1)NC(=N)NC1CCCCCC1 ; Cl]

$^1$H NMR (400 MHz, DMSO-d$_6$) δ 8.08 (br s, 2H), 7.10-7.38 (m, 5H), 6.86 (br s, 2H), 3.66 (m, 1H), 3.33 (m, 4H), 3.15 (m, 2H), 2.77 (m, 2H), 1.81 (m, 2H), 1.36-1.57 (m, 6H); mp 135-137° C.

Example 16: N1,N5-bis(phenethyl) biguanide hydrochloride

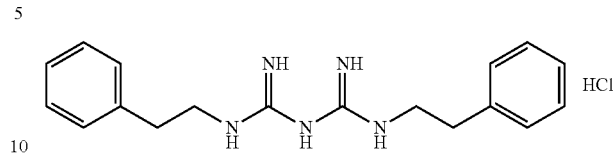

$^1$H NMR (600 MHz, DMSO-d$_6$) δ 8.29 (br s, 2H), 7.34 (m, 2H), 7.26 (m, 3H), 3.00 (t, 2H, 9.0 Hz), 2.92 (t, 2H, J=9.0 Hz); mp 204-205° C.

Example 17: N1,N1,N5-trimethyl biguanide hydrochloride

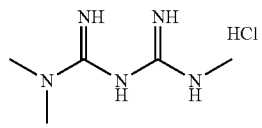

$^1$H NMR (400 MHz, DMSO-d$_6$) δ 7.98 (br s, 2H), 6.91 (br s, 1H), 2.82 (s, 9H); mp 175-177° C.

Example 18: N1,N1-dimethyl-N5-butyl biguanide hydrochloride

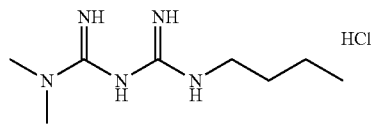

$^1$H NMR (600 MHz, DMSO-d$_6$) δ 7.95 (br s, 2H), 6.93 (br s, 1H), 2.85 (s, 6H), 2.72 (t, 2H, J=7.2 Hz), 1.49 (m, 2H), 1.31 (m, 2H), 0.86 (t, 3H, J=7.8 Hz); mp 131-133° C.

Example 19: N1,N1-dimethyl-N5-(butane-2-yl) biguanide hydrochloride

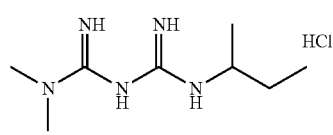

$^1$H NMR (600 MHz, DMSO-d$_6$) δ 7.92 (br s, 2H), 6.94 (br s, 1H), 3.05 (m, 1H), 2.87 (s, 6H), 1.60 (m, 1H), 1.43 (m, 1H), 1.15 (d, 3H, J=5.4 Hz), 0.88 (t, 3H, J=7.2 Hz); mp 110-112° C.

Example 20: N1,N1-dimethyl-N5-t-butyl biguanide hydrochloride

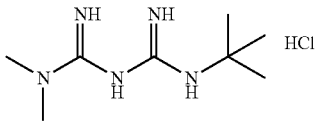

¹H NMR (600 MHz, DMSO-d₆) δ 8.05 (br s, 2H), 6.93 (br s, 1H), 2.85 (s, 6H), 1.23 (s, 9H); mp 186-187° C.

Example 21: N1,N1-dimethyl-N5-pentyl biguanide hydrochloride

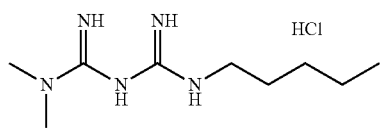

¹H NMR (600 MHz, DMSO-d₆) δ 7.94 (br s, 2H), 6.95 (br s, 1H), 2.86 (s, 6H), 2.73 (t, 2H, J=7.2 Hz), 1.54 (m, 2H), 1.27 (m, 4H), 0.86 (t, 3H, J=7.2 Hz); mp 131-133° C.

Example 22: N1,N1-dimethyl-N5-(methoxycarbonylethyl)biguanide hydrochloride

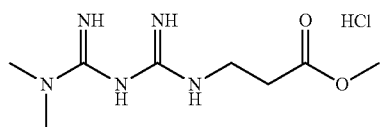

¹H NMR (400 MHz, DMSO-d₆) δ 8.12 (br s, 2H), 6.93 (br s, 1H), 3.61 (s, 3H), 2.97 (t, 2H, J=4.8 Hz), 2.69 (t, 2H, J=4.8 Hz); mp 100-102° C.

Example 23: N1,N1-dimethyl-N5-cycloheptyl biguanide hydrochloride

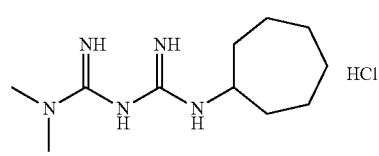 [SMILES: CN(C)C(=N)NC(=N)NC1CCCCCC1 ; Cl]

¹H NMR (400 MHz, DMSO-d₆) δ 8.01 (br s, 2H), 6.93 (br s, 1H), 3.10 (m, 1H), 2.86 (s, 6H), 1.91 (m, 2H), 1.63 (m, 2H), 1.38-1.53 (m, 6H), 1.34 (m, 2H); mp 132-133° C.

Example 24: N1,N1-dimethyl-N5-cyclopropylmethyl biguanide hydrochloride

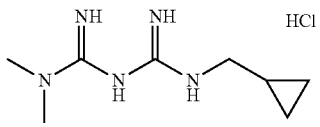

¹H NMR (600 MHz, DMSO-d₆) δ 8.08 (br s, 2H), 6.94 (br s, 1H), 2.86 (s, 6H), 2.63 (d, 2H, J=4.8 Hz), 1.01 (m, 1H), 0.51 (m, 2H), 0.31 (m, 2H); mp 117-118° C.

Example 25: N1,N1-dimethyl-N5-(4-bromo)phenyl biguanide hydrochloride

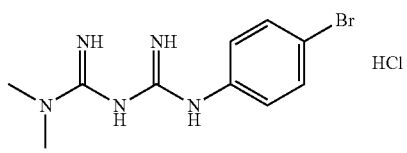 [SMILES: CN(C)C(=N)NC(=N)Nc1ccc(Br)cc1 ; Cl]

¹H NMR (600 MHz, DMSO-d₆) 10.07 (br s, 1H), 7.68 (br s, 2H), 7.40 (d, 2H, J=9.0 Hz), 7.35 (d, 2H, J=9.0 Hz), 2.92 (s, 6H); mp 272-273° C.

Example 26: N1,N1-dimethyl-N5-(furan-2-yl)methyl biguanide hydrochloride

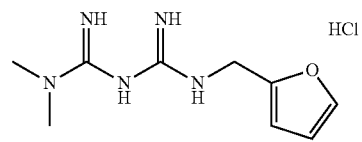

¹H NMR (600 MHz, DMSO-d₆) δ 7.59 (m, 1H), 7.38 (br s, 2H), 6.77 (br s, 1H), 6.40 (dd, 1H, J=2.7, 1.5 Hz), 6.31 (s, 1H), 431 (d, 2H, J=6.0 Hz), 2.92 (s, 6H); mp 176-177° C.

Example 27: N1,N1-dimethyl-N5-(pyridine-3-yl)methyl biguanide hydrochloride

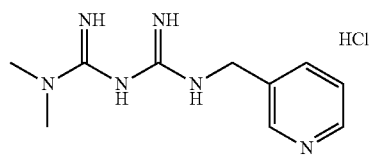 [SMILES: CN(C)C(=N)NC(=N)NCc1cccnc1 ; Cl]

¹H NMR (600 MHz, DMSO-d₆) δ 8.65 (d, 1H, J=1.8 Hz), 8.62 (br s, 2H), 8.52 (dd, 1H, J=4.8, 1.8 Hz), 7.93 (ddd, 1H, J=7.8, 1.8, 1.8 Hz), 7.40 (dd, 1H, J=7.8, 4.8 Hz), 4.01 (s 2H), 3.34 (s, 6H); mp 112-114° C.

Example 28: N1,N1-dimethyl-N5-benzyl biguanide hydrochloride

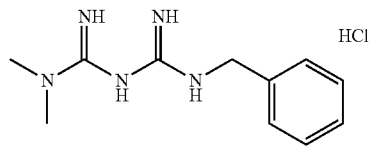 [SMILES: CN(C)C(=N)NC(=N)NCc1ccccc1 ; Cl]

¹H NMR (600 MHz, DMSO-d₆) δ 8.51 (br s, 2H), 7.46 (m, 2H), 7.36 (m, 3H), 6.91 (br s, 1H), 3.95 (s, 2H), 2.83 (s, 6H); mp 151-152° C.

Example 29: N1,N1-dimethyl-N5-(phenethyl) biguanide hydrochloride

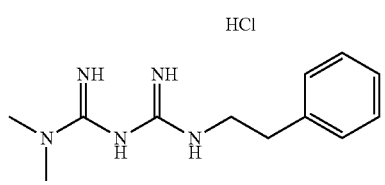 [SMILES: Cl ; CN(C)C(=N)NC(=N)NCCc1ccccc1]

¹H NMR (600 MHz, DMSO-d₆) δ 8.24 (br s, 2H), 7.20-7.34 (m, 6H), 3.00 (t, 2H, J=7.8 Hz), 2.92 (s, 6H), 2.91 (t, 2H, J=7.8 Hz); mp 155-157° C.

Example 30: N1,N1-diethyl-N5-(3-chloro)phenyl biguanide hydrochloride

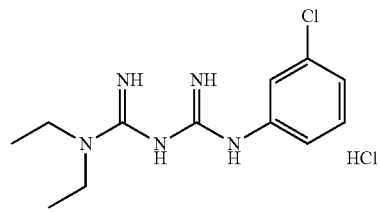 [SMILES: CCN(CC)C(=N)NC(=N)Nc1cccc(Cl)c1 ; Cl]

¹H NMR (400 MHz, DMSO-d₆) δ 9.91 (br s, 1H), 7.64 (br s, 2H), 7.60 (dd, 1H, J=2.0, 2.0 Hz), 7.29 (d, 1H, J=8.0 Hz), 7.26 (ddd, 1H, J=8.0, 1.6, 1.6 Hz), 7.05 (ddd, 1H, J=8.0, 1.6, 1.6 Hz), 6.92 (br s, 1H), 3.31 (m, 4H), 1.08 (m, 6H); mp 219-220° C.

Example 31: N1,N1-dipropyl-N5-(3-chloro)phenyl biguanide hydrochloride

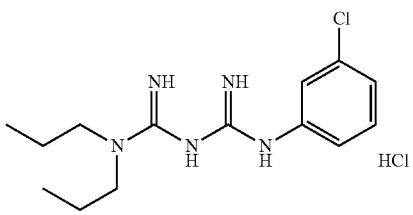 [SMILES: CCCN(CCC)C(=N)NC(=N)Nc1cccc(Cl)c1 ; Cl]

¹H NMR (600 MHz, DMSO-d₆) δ 10.20 (br s, 1H), 7.70 (br s, 2H), 7.63 (d, 1H, J=1.8 Hz), 7.30 (m, 2H), 7.05 (d, 1H, J=7.8 Hz), 3.27 (m, 4H), 1.56 (m, 4H), 0.85 (m, 6H); mp 201-202° C.

Example 32: N1,N1-(ethyl)(propyl)-N5-(4-chloro)phenyl biguanide hydrochloride

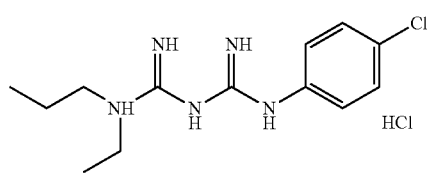 [SMILES: CCCN(CC)C(=N)NC(=N)Nc1ccc(Cl)cc1 ; Cl]

¹H NMR (600 MHz, DMSO-d₆) δ 9.71 (br s, 1H), 8.69 (br s, 1H), 7.42 (d, 2H, J=6.6 Hz), 7.35 (d, 2H, J=6.6 Hz), 7.23 (br s, 2H), 2.90 (q, 2H, J=7.2 Hz), 2.80 (t, 2H, J=7.2 Hz), 1.61 (m, 2H), 1.18 (t, 3H, J=7.2 Hz), 0.91 (t, 3H, J=7.2 Hz); mp 110-112° C.

Example 33: N1,N1-dipropyl-N5-(isoquinoline-5-yl) biguanide hydrochloride

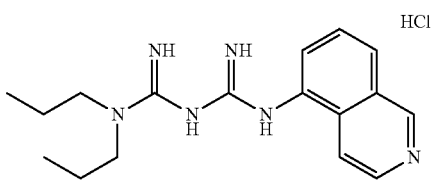 [SMILES: Cl ; CCCN(CCC)C(=N)NC(=N)Nc1cccc2cnccc12]

¹H NMR (400 MHz, DMSO-d₆) 9.27 (br s, 2H), 8.64 (d, 1H, J=8.4 Hz), 7.97 (m, 2H), 7.78 (ddd, 1H, J=8.4, 6.0, 2.4 Hz), 7.71 (d, 1H, J=7.2 Hz), 7.38 (br s, 1H), 7.23 (d, 1H, J=7.2 Hz), 3.21 (t, 2H, J=7.6 Hz), 0.85 (t, 3H, J=7.2 Hz); mp 191-192° C.

Example 34: N1,N1-dihexyl-N5-(3-chloro)phenyl biguanide hydrochloride

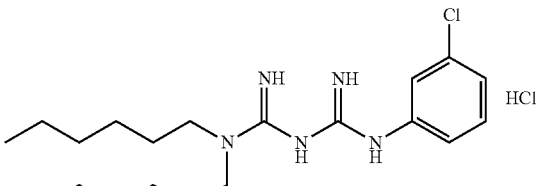

¹H NMR (600 MHz, DMSO-d₆) δ 10.07 (br s, 1H), 7.67 (br s, 1H), 7.62 (dd, 1H, J=2.4, 1.8 Hz), 7.29 (dd, 1H, J=7.8, 7.8 Hz), 7.25 (ddd, 1H, J=7.8, 1.8, 1.2 Hz), 7.05 (ddd, 1H, J=7.8, 2.4, 1.2 Hz) 3.27 (t, 4H, J=7.8 Hz), 1.52 (m, 4H), 1.18-1.34 (m, 12H), 0.82 (m, 6H); mp 187-188° C.

Example 35: N1,N1,N5,N5-tetraethyl biguanide hydrochloride

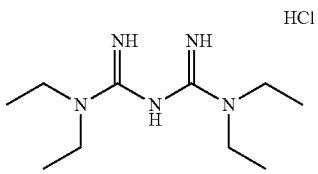

$^1$H NMR (600 MHz, DMSO-$d_6$) δ 8.76 (br s, 2H), 6.90 (br s, 1H), 2.87 (q, 8H, J=7.2 Hz), 1.17 (t, 12H, J=7.2 Hz); mp 140-141° C.

Example 36: N1,N1-diethyl-N5,N5-(cyclohexyl)(methyl) biguanide hydrochloride

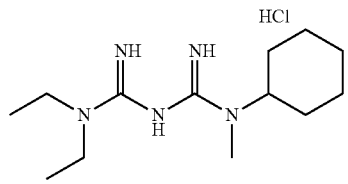 [SMILES: Cl ; CCN(CC)C(=N)NC(=N)N(C)C1CCCCC1]

$^1$H NMR (600 MHz, DMSO-$d_6$) δ 8.73 (br s, 2H), 6.90 (br s, 1H), 3.26 (q, 4H, J=7.2 Hz), 2.86 (m, 1H), 2.49 (s, 3H), 1.99 (m, 2H), 1.74 (m, 2H), 1.20-1.30 (m, 6H), 1.02 (t, 6H, J=7.2 Hz); mp 115-117° C.

Example 37: N1,N1-dipropyl-N5,N5-diethyl biguanide hydrochloride

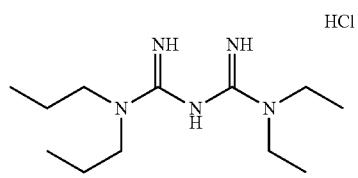 [SMILES: Cl ; CCCN(CCC)C(=N)NC(=N)N(CC)CC]

$^1$H NMR (600 MHz, DMSO-$d_6$) δ 6.92 (br s, 1H), 6.89 (br s, 1H), 3.30 (m, 4H), 3.21 (m, 4H), 1.51 (m, 4H), 1.08 (t, 6H, J=6.0 Hz), 0.84 (t, 6H, J=6.6 Hz); mp 151-152° C.

Example 38: N1,N1-dipropyl-N5,N5-(methyl)(phenethyl) biguanide hydrochloride

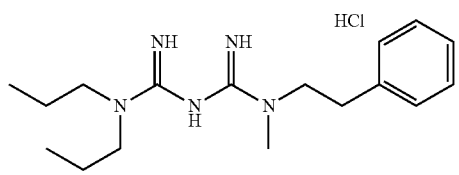 [SMILES: CCCN(CCC)C(=N)NC(=N)N(C)CCc1ccccc1 ; Cl]

$^1$H NMR (600 MHz, DMSO-$d_6$) δ 7.16-7.30 (m, 5H), 6.90 (br s, 2H), 3.47 (t, 2H, J=7.8 Hz), 3.18 (t, 4H, J=7.2 Hz), 2.84 (s, 3H), 2.76 (t, 2H, J=7.8 Hz), 1.49 (m, 4H), 0.83 (m, 6H); mp 110-111° C.

Example 39: N1,N1-dipropyl-N5,N5-(4-hydroxylphenyl)(phenyl) biguanide hydrochloride

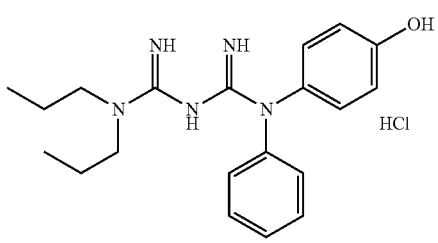 [SMILES: CCCN(CCC)C(=N)NC(=N)N(c1ccccc1)c1ccc(O)cc1 ; Cl]

$^1$H NMR (600 MHz, DMSO-$d_6$) δ 9.86 (br s, 1H), 7.20-7.38 (m, 5H), 7.16 (d, 2H, J=8.4 Hz), 6.84 (br s, 2H), 6.81 (d, 2H, J=8.4 Hz), 3.10 (t, 4H, J=5.4 Hz), 1.54 (m, 4H), 0.89 (t, 6H, J=7.2 Hz); mp 189-190° C.

Example 40: N1,N1,N5,N5-bis((benzyl)(methyl)) biguanide hydrochloride

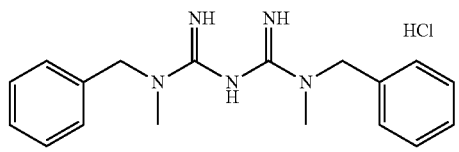 [SMILES: CN(Cc1ccccc1)C(=N)NC(=N)N(C)Cc1ccccc1 ; Cl]

$^1$H NMR (600 MHz, DMSO-$d_6$) δ 7.59 (m, 4H), 7.41 (m, 6H), 7.00 (br s, 2H), 4.07 (s, 4H), 2.47 (s, 6H); mp 141-142° C.

EXPERIMENTAL EXAMPLES

The compounds synthesized by the method described in the examples of the present invention were treated to cancer cells, according to a method to be described in the following Experimental Examples, to measure an effect on inhibition of cancer cell proliferation. A simple experimental method is as follows:

Experimental Example 1: Measurement of Effect on Inhibition of Cancer Cell Proliferation HCT116 cells derived from human colorectal cancer were used, and an effect of a biguanide derivative on the inhibition of cancer cell proliferation was confirmed by measuring a concentration value (cell growth inhibition concentration, GIC50) at which 50% of the cell growth was inhibited using a 3-(4,5-dimethylthiazol-2-yl)-2,5-diphenytetrazolium bromide (MTT) reagent.

First, HCT116 cells were put on a 96-well plate and cultured in a DMEM medium containing 10% bovine serum for 24 hours to each have cell count of approximately 5000. Subsequently, to obtain the G1050 value of each compound, 100 μM (or 200 μM), 25 μM, 6.25 μM, 1.56 μM or 0.39 μM of the compound was treated to each culture medium and then incubated for 48 hours. To confirm living cells after treatment with the compound, MTT was added to each culture medium and further incubated for 3 hours. Generated formazane crystal was dissolved using dimethyl sulfoxide (DMSO) and absorbance of the solution was measured at 560 nm. After the 48-hour incubation, a ratio of a cell count cultured on a well plate not treated with the compound to a cell mount on a well plate treated with compounds synthesized in the examples was indicated as cell viability (%) according to each administered concentration. A cell viability curve was plotted using the cell viability (%), and the calculated concentration value (GIC50) of the compound, at which 50% of the growth was inhibited was, to confirm an effect on the inhibition of cancer cell proliferation.

Results of cancer cell growth inhibition effect are shown in Table 1.

TABLE 1

| Example | GIC50 (uM) @ HCT116 |
|---|---|
| Metformin HCl | 2172 |
| 1 | 23.8 |
| 2 | 20.7 |
| 3 | >100 |
| 4 | 8.4 |
| 5 | 3.2 |
| 6 | >100 |
| 7 | 18.3 |
| 8 | 17.0 |
| 9 | 5.9 |
| 10 | 6.3 |
| 11 | 3.1 |
| 12 | >200 |
| 13 | 47.6 |
| 14 | 47.0 |
| 15 | 17.2 |
| 16 | >100 |
| 17 | >200 |
| 18 | >200 |
| 19 | >200 |
| 20 | >200 |
| 21 | >200 |
| 22 | >200 |
| 23 | >200 |
| 24 | >200 |
| 25 | >100 |
| 26 | >200 |
| 27 | >200 |
| 28 | >200 |
| 29 | >200 |
| 30 | 28.3 |
| 31 | 7.6 |
| 32 | >200 |
| 33 | >100 |
| 34 | 7.8 |
| 35 | >200 |
| 36 | >200 |
| 37 | >100 |
| 38 | 36.0 |
| 39 | >100 |
| 40 | >100 |

Experimental Example 2: Measurement of Effect on AMPK Activation

MCF7 cells derived from human breast cancer cells were used, and an effect of a biguanide derivative on 5'-AMP-activated protein kinase (AMPK) activation was confirmed using an AMPKα immunoassay kit (Invitrogen, catalog No. KHO0651).

The MCF7 cells were put on a 6-well plate and incubated in a DMEM medium containing 10% fetal bovine serum in an incubator to which 5% $CO_2$ was supplied to have a cell count of approximately $5 \times 10^5$. 50 μM of derivatives synthesized in the examples were treated to the each culture medium, and the cells were incubated for 24 hours. Subsequently, the cells were lysed by a method presented in the operation manual of the AMPKα immunoassay kit, and 20 μg of cell lysates were yielded through protein assay. A degree of phosphorylation of an AMPKα threonine $172^{nd}$ residue (Thr172) from the cell lysates were confirmed according to a method presented in the operation manual of the AMPKα immunoassay kit to thereby obtain results. A degree of the AMPKα activation by a biguanide derivative was exhibited as a degree of phosphorylated AMPKα in the cells cultured in the presence of the compounds synthesized in the examples based on phosphorylated AMPKα in cells cultured without treating the biguanide derivative.

In addition, an experiment was performed in the same manner as described in Experimental Example 2 using metformin as a control group, and the results of an effect on AMPK activation were compared to the effect on AMPK activation when 1 mM metformin was treated.

The results are shown in Table 2.

TABLE 2

| | AMPK Activation | | |
|---|---|---|---|
| Example | 0 | 50 μM | fold |
| Metformin HCl | 6.8 | 21.5 (@ 1 mM) | 3.2 |
| 1 | 5.3 | 35.6 | 6.7 |
| 2 | 5.3 | 29.3 | 5.5 |
| 3 | 6.8 | 13.1 | 1.9 |
| 4 | 2.5 | 15.5 | 6.2 |
| 5 | | N.D | |
| 6 | 6.8 | 4.6 | 0.7 |
| 7 | | N.D | |
| 8 | | N.D | |
| 9 | | N.D | |
| 10 | | N.D | |
| 11 | | N.D | |
| 12 | 5.3 | 7.8 | 1.5 |
| 13 | 5.3 | 36.2 | 6.8 |
| 14 | 5.3 | 31.2 | 5.9 |
| 15 | 4.6 | 7.0 | 1.5 |
| 16 | 6.8 | 4.7 | 0.7 |
| 17 | 4.9 | 5.5 | 1.1 |
| 18 | 5.3 | 4.6 | 0.9 |
| 19 | 5.3 | 3.6 | 0.7 |
| 20 | 5.3 | 4.6 | 0.9 |
| 21 | 5.3 | 5.6 | 1.1 |
| 22 | 5.3 | 3.2 | 0.6 |
| 23 | 5.3 | 5.4 | 1.0 |
| 24 | 5.3 | 5.1 | 1.0 |
| 25 | 5.3 | 23.1 | 4.4 |
| 26 | 5.3 | 8.9 | 1.7 |
| 27 | 5.3 | 4.6 | 0.9 |
| 28 | 4.9 | 5.9 | 1.2 |
| 29 | 5.3 | 14.7 | 2.8 |
| 30 | 2.5 | 19.3 | 7.7 |
| 31 | | N.D | |
| 32 | 5.3 | 5.2 | 1.0 |
| 33 | 6.8 | 11.3 | 1.7 |
| 34 | | N.D | |
| 35 | 5.3 | 3.8 | 0.7 |
| 36 | 5.3 | 4.5 | 0.8 |
| 37 | 5.3 | 33.3 | 6.3 |
| 38 | 5.3 | 35.8 | 6.8 |
| 39 | 6.8 | 28.8 | 4.2 |
| 40 | 6.8 | 11.3 | 1.7 |

Consequently, it was seen that the derivatives synthesized in the examples effectively inhibited the viability of cancer cells, particularly, colorectal cancer cells in terms of the effect on inhibition of cancer cell proliferation. In addition, it could be observed that the compounds exhibiting a greater effect on AMPKα activation at a concentration 20 times lower than the control group, metformin, may have an effect at least 20 times greater than the control group.

The invention claimed is:

1. A method of inhibiting of the proliferation of cancer cells, wherein the cancer is breast cancer, colorectal cancer, gastric cancer, liver cancer, lung cancer, blood cancer, prostate cancer, brain cancer, pancreatic cancer, ovarian cancer, or endometrial cancer, the method comprising: administering a therapeutically effective amount of a compound of Formula 1 below or a pharmaceutically acceptable salt to a subject in need thereof:

[Formula 1]

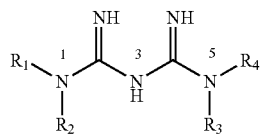

wherein $R_1$ is $C_{5-12}$ aryl, or $C_{1-12}$ alkyl unsubstituted or substituted with $C_{5-12}$ aryl, and the aryl is unsubstituted or substituted with at least one non-hydrogen substituent selected from the group consisting of $C_{1-4}$ alkyl, $C_{1-4}$ alkoxy, hydroxyl, and halogen;

$R_2$ is hydrogen, or $C_{1-12}$ alkyl unsubstituted or substituted with at least one non-hydrogen substituent selected from the group consisting of $C_{3-10}$ cycloalkyl, $C_{5-12}$ aryl, $C_{5-12}$ heteroaryl, hydroxyl, halogen, and $C_{1-4}$ alkoxycarbonyl, and the aryl and heteroaryl are unsubstituted or substituted with at least one non-hydrogen substituent selected from the group consisting of $C_{1-4}$ alkyl, $C_{1-4}$ alkoxy, hydroxyl, and halogen;

$R_3$ is hydrogen, $C_{5-12}$ aryl, or $C_{1-12}$ alkyl unsubstituted or substituted with at least one non-hydrogen substituent selected from the group consisting of $C_{3-10}$ cycloalkyl, $C_{5-12}$ aryl, $C_{5-12}$ heteroaryl, hydroxyl, halogen, and $C_{1-4}$ alkoxycarbonyl, and the aryl and heteroaryl are unsubstituted or substituted with at least one non-hydrogen substituent selected from the group consisting of $C_{1-4}$ alkyl, $C_{1-4}$ alkoxy, hydroxyl, and halogen; and $R_4$ is $C_{3-10}$ cycloalkyl, $C_{1-12}$ alkoxy, $C_{5-12}$ aryl, $C_{5-12}$ heteroaryl, hydroxyl, halogen, or $C_{1-12}$ alkyl unsubstituted or substituted with at least one non-hydrogen substituent selected from the group consisting of $C_{3-10}$ cycloalkyl, $C_{5-12}$ aryl, $C_{5-12}$ heteroaryl, hydroxyl, halogen, and $C_{1-4}$ alkoxycarbonyl, and the aryl and heteroaryl are unsubstituted or substituted with at least one non-hydrogen substituent selected from the group consisting of $C_{1-4}$ alkyl, $C_{1-4}$ alkoxy, hydroxyl, and halogen.

2. The method of claim 1, wherein $R_1$ is $C_{5-12}$ aryl, unsubstituted $C_{1-7}$ alkyl, or $C_{1-6}$ alkyl substituted with $C_{5-12}$ aryl, and the aryl is unsubstituted or substituted with at least one non-hydrogen substituent selected from the group consisting of $C_{1-4}$ alkyl, $C_{1-4}$ alkoxy, hydroxyl, and halogen;

$R_2$ is hydrogen, unsubstituted $C_{1-7}$ alkyl, or $C_{1-6}$ alkyl substituted with at least one non-hydrogen substituent selected from the group consisting of unsubstituted $C_{3-7}$ cycloalkyl, $C_{5-12}$ aryl, $C_{5-12}$ heteroaryl, hydroxyl, halogen, and $C_{1-4}$ alkoxycarbonyl, and the aryl and heteroaryl are unsubstituted or substituted with at least one non-hydrogen substituent selected from the group consisting of $C_{1-4}$ alkyl, $C_{1-4}$ alkoxy, hydroxyl, and halogen;

$R_3$ is hydrogen, $C_{5-12}$ aryl, unsubstituted $C_{1-7}$ alkyl, or $C_{1-6}$ alkyl substituted with at least one non-hydrogen substituent selected from the group consisting of unsubstituted $C_{3-7}$ cycloalkyl, $C_{5-12}$ aryl, $C_{5-12}$ heteroaryl, hydroxyl, halogen, and $C_{1-4}$ alkoxycarbonyl, and the aryl and heteroaryl are unsubstituted or substituted with at least one non-hydrogen substituent selected from the group consisting of $C_{1-4}$ alkyl, $C_{1-4}$ alkoxy, hydroxyl, and halogen; and $R_4$ is unsubstituted $C_{3-7}$ cycloalkyl, $C_{1-6}$ alkoxy, $C_{5-12}$ aryl, $C_{5-12}$ heteroaryl, hydroxyl, halogen, unsubstituted $C_{1-7}$ alkyl, or $C_{1-6}$ alkyl substituted with at least one non-hydrogen substituent selected from the group consisting of unsubstituted $C_{3-7}$ cycloalkyl, $C_{5-12}$ aryl, $C_{5-12}$ heteroaryl, hydroxyl, halogen, and $C_{1-4}$ alkoxycarbonyl, and the aryl and heteroaryl are unsubstituted or substituted with at least one non-hydrogen substituent selected from the group consisting of $C_{1-4}$ alkyl, $C_{1-4}$ alkoxy, hydroxyl, and halogen.

3. The method of claim 2, wherein $R_1$ is $C_{5-12}$ aryl, unsubstituted $C_{1-7}$ alkyl, or $C_{1-6}$ alkyl substituted with $C_{5-12}$ aryl, and the aryl is unsubstituted or substituted with at least one non-hydrogen substituent selected from the group consisting of $C_{1-4}$ alkyl, $C_{1-4}$ alkoxy, hydroxyl, and halogen;

$R_2$ is hydrogen, unsubstituted $C_{1-7}$ alkyl, or $C_{1-6}$ alkyl substituted with $C_{5-12}$ heteroaryl, and the heteroaryl is unsubstituted or substituted with at least one non-hydrogen substituent selected from the group consisting of $C_{1-4}$ alkyl, $C_{1-4}$ alkoxy, hydroxyl, and halogen;

$R_3$ is hydrogen, $C_{5-12}$ aryl, unsubstituted $C_{1-7}$ alkyl, or $C_{1-6}$ alkyl substituted with $C_{5-12}$ heteroaryl, and the aryl and heteroaryl are unsubstituted or substituted with at least one non-hydrogen substituent selected from the group consisting of $C_{1-4}$ alkyl, $C_{1-4}$ alkoxy, hydroxyl, and halogen; and $R_4$ is unsubstituted $C_{3-7}$ cycloalkyl, $C_{5-12}$ aryl, $C_{5-12}$ heteroaryl, unsubstituted $C_{1-7}$ alkyl, or $C_{1-6}$ alkyl substituted with at least one non-hydrogen substituent selected from the group consisting of unsubstituted $C_{3-7}$ cycloalkyl, $C_{5-12}$ aryl, $C_{5-12}$ heteroaryl, and $C_{1-4}$ alkoxycarbonyl, and the aryl and heteroaryl are unsubstituted or substituted with at least one non-hydrogen substituent selected from the group consisting of $C_{1-4}$ alkyl, $C_{1-4}$ alkoxy, hydroxyl, and halogen.

4. The method of claim 3, wherein $R_1$ is $C_{5-12}$ aryl, unsubstituted $C_{1-7}$ alkyl, or $C_{1-4}$ alkyl substituted with $C_{5-12}$ aryl, and the aryl is unsubstituted or substituted with at least one non-hydrogen substituent selected from the group consisting of $C_{1-4}$ alkyl, $C_{1-4}$ alkoxy, hydroxyl, and halogen;

$R_2$ is hydrogen, unsubstituted $C_{1-7}$ alkyl, or $C_{1-4}$ alkyl substituted with $C_{5-12}$ heteroaryl, and the heteroaryl may be unsubstituted or substituted with at least one non-hydrogen substituent selected from the group consisting of $C_{1-4}$ alkoxy, hydroxyl, and halogen, and the heteroaryl is selected from the group consisting of pyridinyl, furanyl, and isoquinolinyl;

$R_3$ is hydrogen, $C_{5-12}$ aryl, unsubstituted $C_{1-7}$ alkyl, or $C_{1-4}$ alkyl substituted with $C_{5-12}$ heteroaryl, and the aryl and heteroaryl may be unsubstituted or substituted with at least one non-hydrogen substituent selected from the group consisting of $C_{1-4}$ alkoxy, hydroxyl, and halogen, and the aryl and heteroaryl is selected from the group consisting of phenyl, pyridinyl, furanyl, and isoquinolinyl; and $R_4$ is unsubstituted $C_{3-7}$ cycloalkyl, $C_{5-12}$ aryl, $C_{5-12}$ heteroaryl, unsubstituted $C_{1-7}$ alkyl, or $C_{1-4}$ alkyl substituted with at least one non-hydrogen substituent selected from the group consisting of unsubstituted $C_{3-7}$ cycloalkyl, $C_{5-12}$ aryl, $C_{5-12}$ heteroaryl, and $C_{1-4}$ alkoxycarbonyl, and the aryl and heteroaryl are unsubstituted or substituted with at least one non-hydrogen substituent selected from the group consisting of $C_{1-4}$ alkyl, $C_{1-4}$ alkoxy, hydroxyl, and halogen.

5. The method of claim 4, wherein $R_1$ is $C_{5-12}$ aryl, unsubstituted $C_{1-7}$ alkyl, or $C_{1-6}$ alkyl substituted with $C_{5-12}$ aryl;

$R_2$ is hydrogen, $C_{5-12}$ aryl, or unsubstituted $C_{1-7}$ alkyl;

$R_3$ is hydrogen, $C_{5-12}$ aryl, or unsubstituted $C_{1-7}$ alkyl; and $R_4$ is unsubstituted $C_{3-7}$ cycloalkyl, $C_{5-12}$ aryl, $C_{5-12}$ heteroaryl, unsubstituted $C_{1-7}$ alkyl, or $C_{1-4}$ alkyl substituted with at least one non-hydrogen substituent selected from the group consisting of unsubstituted $C_{3-7}$ cycloalkyl, $C_{5-12}$ aryl, $C_{5-12}$ heteroaryl, and $C_{1-4}$ alkoxycarbonyl; and the aryl and heteroaryl may be unsubstituted or substituted with at least one non-hydrogen substituent selected from the group consisting of $C_{1-4}$ alkoxy, hydroxyl, and halogen, and the aryl and heteroaryl is selected from the group consisting of phenyl, pyridinyl, furanyl, and isoquinolinyl.

6. The method of claim 1, wherein the compound of Formula 1 is

N1-hexyl-N5-propyl biguanide;
N1-hexyl-N5-cyclopropylmethyl biguanide;
N1-hexyl-N5-cyclohexylmethyl biguanide;
N1-hexyl-N5-benzyl biguanide;
N1,N5-bis(4-chlorophenyl) biguanide;
N1,N5-bis(3-chlorophenyl) biguanide;
N1-(4-chloro)phenyl-N5-(4-methoxy)phenyl biguanide;
N1,N5-bis(3-chloro-4-methoxyphenyl) biguanide;
N1,N5-bis(3,4-dichlorophenyl) biguanide;
N1,N5-bis(3,5-dichlorophenyl) biguanide;
N1,N5-bis(4-bromophenyl) biguanide;
N1-benzyl-N5-(pyridine-3-yl)methyl biguanide;
N1-(phenethyl)-N5-propyl biguanide;
N1-(phenethyl)-N5-cyclopropylmethyl biguanide;
N1-(phenethyl)-N5-cycloheptyl biguanide;
N1,N5-bis(phenethyl) biguanide;
N1,N1,N5-trimethyl biguanide;
N1,N1-dimethyl-N5-butyl biguanide;
N1,N1-dimethyl-N5-(butan-2-yl) biguanide;
N1,N1-dimethyl-N5-t-butyl biguanide;
N1,N1-dimethyl-N5-pentyl biguanide;
N1,N1-dimethyl-N5-methoxycarbonylethyl biguanide;
N1,N1-dimethyl-N5-cycloheptyl biguanide;
N1,N1-dimethyl-N5-cyclopropylmethyl biguanide;
N1,N1-dimethyl-N5-(4-bromo)phenyl biguanide;
N1,N1-dimethyl-N5-(furan-2-yl)methyl biguanide;
N1,N1-dimethyl-N5-(pyridine-3-yl)methyl biguanide;
N1,N1-dimethyl-N5-benzyl biguanide;
N1,N1-dimethyl-N5-(phenethyl) biguanide;
N1,N1-diethyl-N5-(3-chloro)phenyl biguanide;
N1,N1-dipropyl-N5-(3-chloro)phenyl biguanide;
N1,N1-(ethyl)(propyl)-N5-(4-chloro)phenyl biguanide;
N1,N1-dipropyl-N5-(isoquionline-5-yl) biguanide;
N1,N1-dihexyl-N5-(3-chloro)phenyl biguanide;
N1,N1,N5,N5-tetraethyl biguanide;
N1,N1-diethyl-N5,N5-(cyclohexyl)(methyl) biguanide;
N1,N1-dipropyl-N5,N5-diethyl biguanide;
N1,N1-dipropyl-N5,N5-(methyl)(phenethyl) biguanide;
N1,N1-dipropyl-N5,N5-(4-hydroxylphenyl)(phenyl) biguanide; or
N1,N1,N5,N5-bis((benzyl)(methyl)) biguanide.

7. The method of claim 1, wherein the pharmaceutically acceptable salt is a salt with an acid selected from the group consisting of formic acid, acetic acid, propionic acid, lactic acid, butyric acid, isobutyic acid, trifluoroacetic acid, malic acid, maleic acid, malonic acid, fumaric acid, succinic acid, succinic acid monoamide, glutamic acid, tartaric acid, oxalic acid, citric acid, glycolic acid, glucuronic acid, ascorbic acid, benzoic acid, phthalic acid, salicylic acid, anthranyl acid, benzensulfonic acid, p-toluenesulfonic acid, methanesulfonic acid, dichloroacetic acid, aminooxy acetic acid, hydrochloric acid, bromic acid, sulfuric acid, phosphoric acid, nitric acid, carbonic acid, and boric acid.

* * * * *